(12) United States Patent
Zhang et al.

(10) Patent No.: US 10,408,804 B2
(45) Date of Patent: Sep. 10, 2019

(54) DARKROOM TYPE SECURITY INSPECTION APPARATUS AND METHOD

(71) Applicants: TSINGHUA UNIVERSITY, Beijing (CN); NUCTECH COMPANY LIMITED, Beijing (CN)

(72) Inventors: Qingjun Zhang, Beijing (CN); Yuanjing Li, Beijing (CN); Zhiqiang Chen, Beijing (CN); Ziran Zhao, Beijing (CN); Weiping Zhu, Beijing (CN); Yaohong Liu, Beijing (CN); Qiufeng Ma, Beijing (CN); Xiang Zou, Beijing (CN); Huishao He, Beijing (CN); Jianping Chang, Beijing (CN); Song Liang, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 169 days.

(21) Appl. No.: 15/276,595

(22) Filed: Sep. 26, 2016

(65) Prior Publication Data

US 2017/0138914 A1    May 18, 2017

(30) Foreign Application Priority Data

Nov. 18, 2015   (CN) .......................... 2015 1 0796132

(51) Int. Cl.
*G01N 30/72* (2006.01)
*G01N 23/085* (2018.01)
*G01B 15/00* (2006.01)
*G01N 30/84* (2006.01)

(52) U.S. Cl.
CPC ......... *G01N 30/7206* (2013.01); *G01B 15/00* (2013.01); *G01N 23/085* (2018.02); *G01N 2030/8452* (2013.01)

(58) Field of Classification Search
CPC .................................................. G01N 30/7206
USPC ....................................................... 73/23.37
See application file for complete search history.

(56) References Cited

U.S. PATENT DOCUMENTS

2015/0233796 A1* 8/2015 Kashima ............. H01J 49/0422
                                                      250/288

* cited by examiner

*Primary Examiner* — Justin Seo
*Assistant Examiner* — Jean F Morello
(74) *Attorney, Agent, or Firm* — Pillsbury Winthrop Shaw Pittman LLP

(57) ABSTRACT

A darkroom type security inspection apparatus and a method of performing an inspection using the darkroom type security inspection apparatus. An apparatus includes a housing constituting a closed darkroom, and assemblies disposed inside the housing. The assemblies disposed inside the housing include: a sample collecting unit configured to collect a sample, a conveyor unit, and a X-ray detection unit to detect a position of the objected to be inspected, wherein the X-ray detection unit is configured to determine the position of the objected to be inspected within the sampling assembly so that the object to be inspected together with the conveyor unit is conveyed to an expected position; and a sample processing assembly, wherein the assemblies disposed inside the housing are communicated by fittings or connectors.

20 Claims, 5 Drawing Sheets

DARKROOM TYPE SECURITY INSPECTION APPARATUS AND METHOD

TECHNICAL FIELD

The present invention relates to the field of security inspection technology, and in particular, to darkroom type security inspection apparatus and method based on IMS and its associated technologies.

BACKGROUND

In today's society, science and technology change rapidly, and economic globalization continues to develop. Terrorist attacks, food safety, medical security, drug trafficking and other serious social problems threaten people's lives and property, health and safety. In order to maintain the normal social order and protect peoples' lives, property, health and safety, in recent years, detection technology and related equipment based on various detection principles have developed rapidly.

Ion mobility spectrometry (IMS) technology, due to its characteristics of simple structure, high sensitivity, and rapid analysis, is widely used for detection and monitoring of chemical warfare agents, drugs, explosives and other aspects of environmental monitoring.

Due to the excellent performance of IMS, a variety of equipment and technologies based on IMS technology and its related associated technologies have gradually emerged in the detection fields of foods, cosmetics and pharmaceutical health. The Gas chromatography-ion mobility spectrometry (GC-IMS) associated technology with its full use of the separation characteristics of the GC, rapid response, and high sensitivity of the IMS, not only effectively solves both low discriminative ability of the GC and a cross sensitivity problem of IMS during detection of a mixture, but also can obtain a retention time, drift time of an object to be detected in a migration passage, and signal strength of the object to be detected inducted in the Faraday disc, so that obtained 3D map information of the object can be used to perform an effective and accurate recognition. In the future, GC-IMS detection technology will strongly apply to the fields of riots, terrorism, drug trafficking, environmental monitoring, food safety, medical supervision and health, and the like.

SUMMARY

However, traditional IMS and its associated equipment mainly are in the form of handheld, portable, benchtop, door-type, etc. In the practical applications, they are inconvenient in sampling, resulting in low detection efficiency, or an object to be detected needs to be destroyed. And, an object to be detected such as baggage needs to be unpacked, which is very inconvenient.

It is desired, for example, that a product using IMS or associated technology has high sampling efficiency, high collecting speed, and high accuracy without destructive sampling, and can realize fast on-site inspection without unpacking. Moreover, it is expected that an apparatus, which has characteristics of chemical detection and strong detection capability for rapid detection of goods of various sizes, can be used in an existing customs framework and in other situations.

Embodiments of the present invention provide a security inspection apparatus and a method, which overcome at least one of the abovementioned problems and can perform on-site sampling inspection accurately and rapidly without any destruction.

According to an aspect, there is provided a darkroom type security inspection apparatus comprising: a housing constituting a closed darkroom, and assemblies disposed inside the housing, the assemblies disposed inside the housing comprising:

a sampling assembly comprising a sample collecting unit configured to collect a sample, a conveyor unit configured to convey an object to be inspected from outside into the sample collecting unit, and a X-ray detection unit to detect a position of the objected to be inspected, wherein the X-ray detection unit is configured to determine the position of the objected to be inspected within the sampling assembly so that the objected to be inspected together with the conveyor unit is conveyed to an expected position;

a sample processing assembly configured to concentrate and desorb the sample; and a sample inspecting assembly configured to inspect composition of the sample by means of a gas chromatographic-ion mobility spectrometer or a separated ion mobility spectrometer, wherein the sampling assembly, the sample processing assembly and the sample inspecting assembly are communicated by fittings so that collection, processing and inspection of the sample are performed on the object to be inspected, that has been conveyed into the housing constituting the closed darkroom, within the housing.

This darkroom type baggage security inspection apparatus can provide a convenient, rapid and effective sampling and conveying method and a rapid and accurate detection system, to achieve a rapid trace detection without unpacking and destructing the items to be inspected. It is suitable for rapid inspection for drugs, explosives, prohibited volatile chemical agents, solid surface contaminations in airports or customs, and the like.

In order to achieve one or more of the above technical objects, technical solutions can be achieved as follows: the present embodiments are suitable for darkroom type security inspection apparatus comprising analysis equipment including fast GC-IMS, IMS, GC-IMS-MS or other apparatuses, and provide a related sample collection and concentration method.

BRIEF DESCRIPTION OF THE DRAWINGS

In order to provide a more clear understanding, embodiments will be further described hereinafter in detail and completely with reference to the attached drawings, in which.

Figure 1:
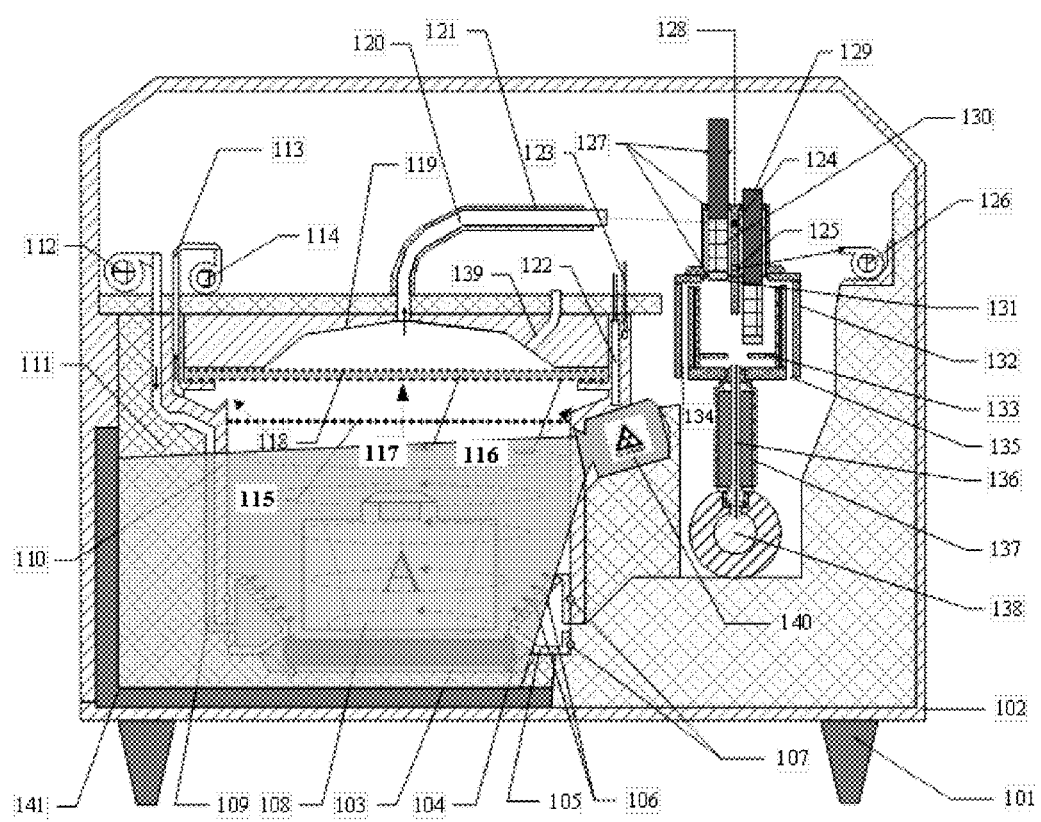
FIG. 1 is a schematic view showing a sampling process of a darkroom type baggage security inspection apparatus according to an embodiment of the present invention.

LIST OF THE NUMBERS IN THE DRAWINGS 101 balance strut;
102 shielding housing of the security inspection apparatus;
103 conveyor belt;
104 conveyor belt brace;
105 eddy flow guiding plate;
106 eddy flow hole;
107 O-ring seal;
108 baggage to be inspected;
109 inflation passage;
110 gas guiding chamber;
111 thermal sleeve;
112 inflating pump;
113 exhaust passage;
114 exhaust pump;
115 heating filter;
116 bottom clamping net;
117 semi-permeable membrane;
118 top clamping net;
119 top tundish-shaped cover;
120 sample collecting connection passage;
121 sample collecting connection passage heating sleeve;
122 heating rod;
123 temperature sensor;
124 sample collection interface;
125 sample suction pump interface;
126 sample suction pump;
127 heat-resistant O-ring seal;
128 piston cylinder;
129 piston rod;
130 absorption sieve drum;
131 thermal insulation pad;
132 thermal desorption chamber;
133 liner passage;
134 carrier gas inlet;
135 shunting/sweeping interface;
136 MCC column;
137 thermal conductive sheath;
138 double-mode ion mobility spectrometer;
139 sample carrier gas interface;
140 X-ray generator;
141 L-shaped array of detectors.

DETAILED DESCRIPTION OF THE EMBODIMENTS

Exemplary embodiments will be described hereinafter in detail with reference to the attached drawings, wherein the like reference numerals refer to the like elements.

Figure 2:
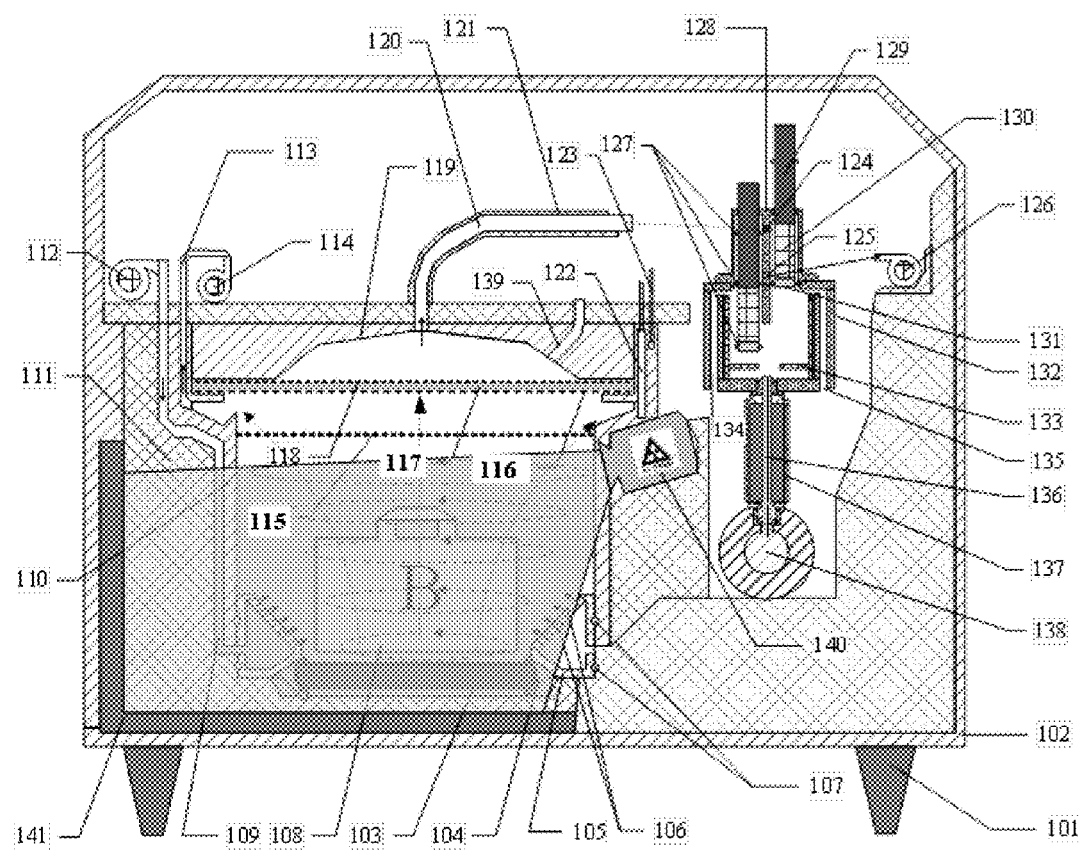
FIG. 2 is a schematic view showing a sample thermally desorbing process of a darkroom type baggage security inspection apparatus according to an embodiment of the present invention.
Figure 3:
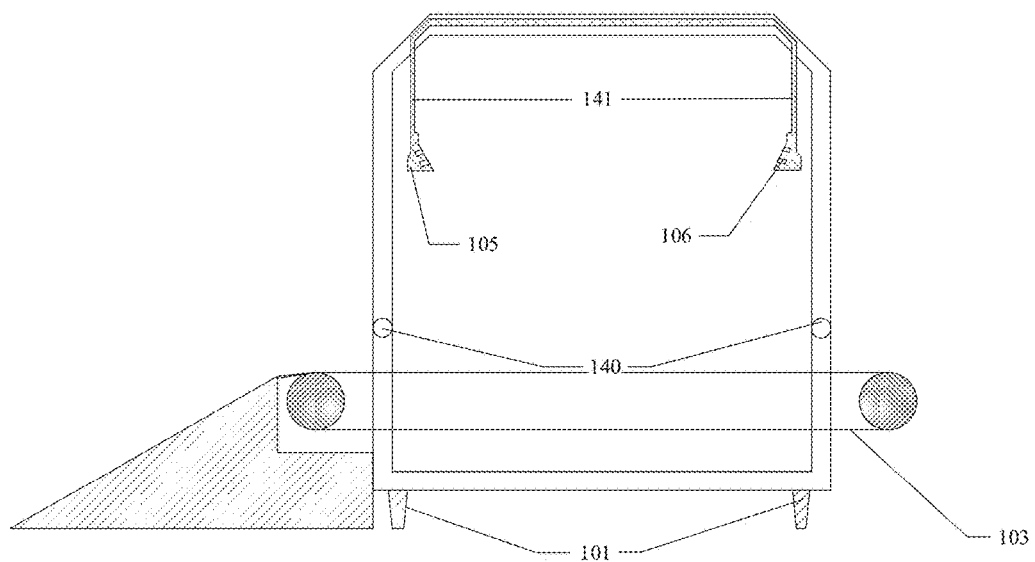
FIG. 3 is a side schematic view of a darkroom type baggage security inspection apparatus according to an embodiment of the present invention.

In accordance with one or more embodiments, a darkroom type security inspection apparatus based on an ion mobility spectrometry (IMS) and its associated technologies, for example, a darkroom type baggage rapid security inspection apparatus (as shown in FIGS. 1 and 2), is provided. The apparatus comprises a housing 102 creating a closed darkroom, and assemblies disposed inside the housing. The assemblies disposed inside the housing comprise a sampling assembly, a sample processing assembly, an X-ray detection assembly and a sample inspection assembly which are communicated by fittings for example including connection tubes or connectors. Alternatively, the X-ray detection assembly may be provided outside the darkroom. In other words, the X-ray detection assembly may be not communicated with other assemblies, which helps to reduce a risk of polluting these communicated assemblies.

Figure 5:
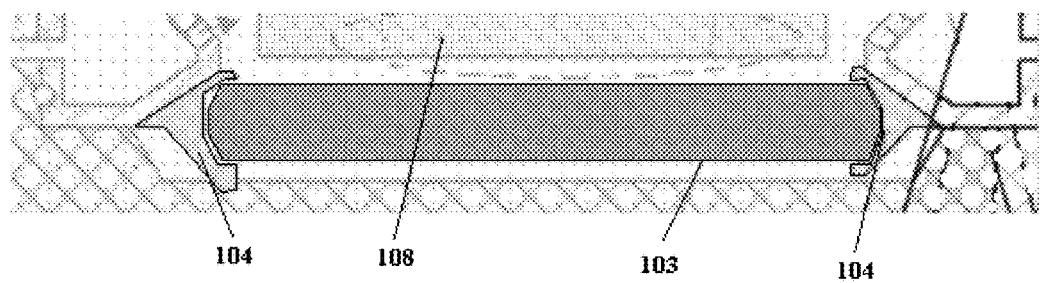
FIG. 5 is a schematic view showing a portion of a darkroom type baggage security inspection apparatus as shown in FIG. 1, namely a portion around belt 103 and brace 104, according to an embodiment of the present invention.

The assemblies disposed inside the housing of the security inspection apparatus comprise a tornado type sampling chamber, a full time pre-concentration sampler, a thermal desorption chamber, a chromatographic column, a thermal insulation unit, an ion mobility spectrometry and the like. In the darkroom type baggage rapid security inspection apparatus, a plurality of balance struts 101 are used to support the housing 102 made of metal and configured for shielding the apparatus body and fixed stands of the security inspection apparatus (the housing has a thickness enough to shield the rays). Desirably, the balance struts comprise rubber-sleeved steel posts having elastic and flexible legs. In the darkroom type baggage rapid security inspection apparatus, a conveyor belt 103 is used to convey a baggage to be inspected 108 and to support the baggage to be inspected 108, and the conveyor belt 103 is driven by a reducing motor. Referring to FIGS. 1 and 5, conveyor belt braces 104 for engagement with the conveyor belt are mounted at both sides of the conveyor belt 103 so that the conveyor belt braces 104 allow the conveyor belt 103 to move but form a seal together with the conveyor belt when the conveyor belt does not move, so as to form a sealed environment inside the whole darkroom. The conveyor belt brace 104 is made of deformable material and comprises an upper limb and a lower limb. When the conveyor belt does not move, a negative pressure is produced so that the conveyor belt braces 104 are deformed to press against the conveyor belt 103 by the upper limb and the lower limb so that external air or other substances will not enter the darkroom through a gap between the conveyor belt 103 and the conveyor belt braces 104, reducing interference of collection, analysis and detection of the sample from external effects. It should be understood by those skilled in the art that other units configured to convey the sample may be provided in accordance with requirements.

According to an embodiment, the sampling assembly of the darkroom type security inspection apparatus comprises an X-ray detection unit. The X-ray detection unit comprises an X-ray generator 140, one or more X-ray detectors and a display.

Specifically, lead shielding curtains are provided at both the entrance door and the exit door of the security inspection apparatus. An infrared sensor is mounted at a side wall of the housing near an entrance door of the security inspection apparatus. When the infrared sensor senses that the baggage to be inspected 108 is completely moved into the security inspection apparatus, the roll-up doors provided at both entrance door and exit door of the housing are rolled down, so that a closed darkroom is formed in the whole security inspection housing. Meanwhile, the motor starts to reduce speed, so that the conveyor belt is decelerated. After that, for example, after about 0.5 second, the X-ray generator 140 begins to emit ray beams, and the L-shaped array of detectors 141 as shown receive the X-ray beams, perform photoelectric conversion, transfer converted signals to a prepositioned amplifier and a main amplifier, perform conversion in an A/D converter, perform digit image processing in a digital image processing unit, and is displayed as a computed tomography image in the display. With the forward movement of the object 108, every cross section of the baggage to be inspected 108 is scanned continuously, and energy values of the X-ray beams adsorbed by these cross sections of the baggage or luggage 108 are recorded. As a result, a whole two-dimensional projection image of the baggage 108 along a direction from the X-ray source to the detectors is obtained. Thereby, contents inside the object to be inspected 108 such as cases and bags are displayed. Meanwhile, a position of the object to be inspected 108 can be determined through the image displayed in the display. When the object to be inspected 108 arrives at an expected position, the conveyor belt stops. In one embodiment, the X-ray detection unit is provided in the sampling assembly, which not only can be used for determining the position of the object to be inspected 108 but also can detect whether or not one or more prohibited items are contained in the object to be inspected 108. In one embodiment, the X-ray detection unit is provided in the sampling assembly, as a result, once the object to be inspected 108 goes into the sampling assembly, a scan is performed on the object to be inspected 108, to observe whether or not one or more prohibited items, for example knives and the like, are contained in the object to be inspected 108, and meanwhile, to judge if the object to be inspected 108 is at an expected position based on the image displayed in the display. In one embodiment, the X-ray detection unit is provided in the sampling assembly, to judge if the object to be inspected 108 is at an expected position based on the image displayed in the display. Once the object to be inspected 108 is at the expected position, the X-ray detection unit performs a scan on the object to be inspected 108, for example, to scan the object to be inspected 108 by X-ray beams emitted by the X-ray generator 140. To scan the object to be inspected 108 by X-ray beams does not adversely affect other samples, other than one or more prohibited items, for example knives and the like, carried in the object to be inspected 108, and these samples will be inspected and judged by the sample inspecting assembly of the security inspection apparatus.

The darkroom type security inspection apparatus comprises the sampling assembly comprising a sample collecting unit and a conveyor unit configured to convey an object to be inspected into an expected position within the sample collecting unit. The sample collecting unit comprises a sampling chamber having a first end and a second end opposite to the first end, the conveyor unit is located at the first end, and the sampling chamber further comprises a sample outlet adjacent to the second end and configured to discharge the sample. The sampling chamber further comprises an inflation port 106 and an exhaust port formed at an inner wall of the sampling chamber, the inflation port 106 is configured to introduce a gas flow and the exhaust port is configured to discharge the gas, so as to produce a tornado type gas flow within the sampling chamber, and the tornado type gas flow moves spirally from the first end to the second end of the sampling chamber so that the sample carried by the object to be inspected is conveyed by the tornado type gas flow to be nearby the second end. It should be understood that the mentioned first and second ends are only used for distinguishing two ends of the sampling chamber, instead of containing any sense on their order or importance.

Figure 4:
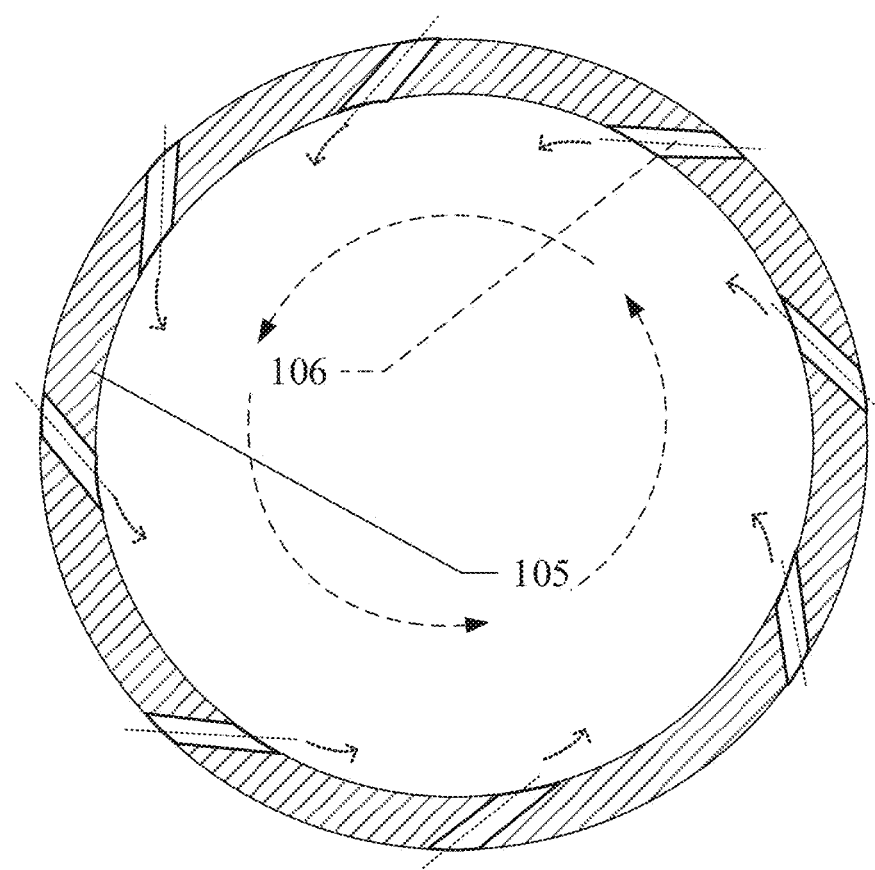
FIG. 4 is a top cross-sectional view of an eddy flow guiding plate (formed as a full circle guiding plate) of a darkroom type baggage security inspection apparatus according to an embodiment of the present invention.

According to one embodiment, an eddy flow guiding plate 105 distributed on side walls of the housing and the roll-up doors form a whole circle, and the inflation port 106 is provided on the eddy flow guiding plate 105, as shown in FIG. 4. The inner wall of the eddy flow guiding plate 105 forms as a portion of the inner wall of the sampling chamber and has its cross section of conical shape shown in FIG. 1, that is, the inner wall of the eddy flow guiding plate 105 and the inner wall of the sampling chamber together form a frustoconical shape having a smaller-diameter round end adjacent to the chamber and a larger-diameter round end adjacent to the second end. The sampling chamber may be in other forms, for example, one or more other portions of the inner wall of the chamber are in a frustoconical shape having a smaller-diameter round end serving as the first end and a larger-diameter round end serving as the second end.

After formation of the darkroom, an inflating pump 112 and an exhaust pump 114 operate. Gas is introduced by the pump 112 into the sampling chamber through the inflation port 106 via the inflation passage 109. The inflation port is configured so that an axially inflating direction of the inflation port is mostly tangent with an inner surface of the inner wall of the chamber and is inclined towards the sample outlet side. The gas flow discharged from the eddy flow hole 106 of the eddy flow guiding plate 105 forms an eddy flow, so as to form a sampling tornado within the darkroom under the action of the pump 112, the pump 114 and a sample suction pump 126.

According to one embodiment, a heating rod 122, a thermal sleeve 111, and a gas guiding chamber 110 protected by the thermal sleeve 111 are provided at a side wall of the housing of the security inspection apparatus. The gas guiding chamber may be a sampling chamber. The tornado or tornado gas flow is heated within the gas guiding chamber 110 and the inflation passage by a heating rod 122 and is thermally insulated by the thermal sleeve 111, to form a heated tornado. Strong suction action of the hot tornado suctions a solid small particulate sample adhered to surface of the baggage to be inspected 108 and a gaseous sample released from one or more volatile or semi-volatile articles packed in the baggage. In addition, the hot tornado helps rapid volatilization of the highly volatile or volatile prohibited item packed in the baggage, facilitating sample collection and detection. The sample suctioned by the hot tornado passes quickly through a heating filter 115 provided inside the gas guiding chamber 110 and is quickly heated by high temperature heating filter 115. The heating filter 115 on one hand prevents large particulates from entering and blocks their passage, and on the other hand heats the sample suctioned by the tornado, particularly it quickly heats the solid small particulate sample and at some of the volatiles. The volatilized sample, together with the highly volatile sample, may pass through the semi-permeable membrane and enter the adsorber and the inspecting assembly, for analysis and detection.

Hot gas flow is discharged through an exhaust passage 113 under the action of the exhaust pump 114. The hot gas flow does not produce a convection below the heating filter 115, effectively avoiding the baggage to be inspected to be heated. Volatilized gas from the highly volatile sample contained in the baggage to be inspected can pass directly through a bottom clamping net 116, a semi-permeable membrane 117 and a top clamping net 118 after passing through the heating filter 115 and enter a space of a top tundish-shaped cover 119. The nonvolatile solid sample volatiles some gaseous sample by the heating of the heating filter 115, and then the volatilized gaseous sample passes through the bottom clamping net 116, the semi-permeable membrane 117 and the top clamping net 118 and enters the space of the top tundish-shaped cover 119. Semi-permeable membranes are provided below the heating filter and the top tundish-shaped cover. The semi-permeable membrane is clamped by two metal sheets which, on one hand, are used for fixation of the semi-permeable membrane and, on the other hand, can prevent the semi-permeable membrane from being torn under the action of the strong tornado. Material for the semi-permeable membrane can selectively filter out substances to be passed through. Material for the semi-permeable membrane can prevent other contaminants including water molecules, ammonia molecules contained in the carrier gas from passing through, so as to avoid pollution of the chromatographic column or the migration passage. In addition, the semi-permeable membrane can also prevent formation of clusters, improving the resolution ratio of the apparatus. The gas guiding chamber of this design allows the apparatus to achieve sampling of volatile, semi-volatile substances and surface contaminations, broadening selectivity to the substance to be inspected.

According to one embodiment, a thermal insulation unit is provided in the sampling passage, effectively preventing condensation of the inhaled samples and pollution of the passage caused by the condensation.

The sample reaching the space of the top tundish-shaped cover 119 and the carrier gas coming from the sample carrier gas interface 139 are mixed in the cover with a loophole and reach the pre-concentrated sample adsorber after passing through a sample collecting connection passage 120 and the sample collection interface 124. A full-time pre-concentrated sample adsorber is used to achieve a full-time collection of the sample, greatly improving detection efficiency of the apparatus.

The mixed gas containing the sample and the carrier gas is firstly conveyed to the sample processing assembly. The sample processing assembly is configured to concentrate and analyze the sample. The sample processing assembly comprises a pre-concentrated sample adsorber comprising an absorption sieve drum configured to concentrate the sample and a piston rod configured to deliver the sample in the absorption sieve drum through a piston, and a thermal desorption chamber configured to desorb the sample in the absorption sieve drum at high temperature and to mix the sample with a suitable carrier gas.

The mixed gas containing the sample is conveyed to the absorption sieve drum 130 of the pre-concentrated sample adsorber and is absorbed by adsorbent in the sieve drum. The sample collecting connection passage 120 has a sample collecting connection passage heating sleeve 121 that is heated to maintain a high temperature in the passage, effectively preventing condensation of the inhaled samples and pollution of the passage caused by the condensation. Under the continuous action of the sample suction pump 126, enrichment and concentration of the sample in the absorption sieve drum 130 can be achieved.

After concentration of the sample, under the action of the motor, the absorption sieve drum 130 is pushed from the piston rod 129 of the piston-type adsorber to the thermal desorption chamber 132. Desirably, the thermal desorption chamber is manufactured of stainless steel and nickel plated copper material with stable chemical properties. Desirably, the pre-concentrated sample adsorber comprises two or more absorption sieve drums, and correspondingly, a plurality of piston rods.

The sample absorbed to the adsorber is rapidly desorbed in the thermal desorption chamber 132 at high temperature, is mixed with a pre-heated carrier gas coming from a carrier gas inlet 134, is brought to a MCC column 136 by the carried gas, and then a pre-separation is performed in the MCC column 136. After performing the pre-separation, the sample is guided to the double-mode ion mobility spectrometer 138, for detection and analysis. Use of the technology of double-mode ion mobility spectrometry achieves on-site detection of the positive and negative ions of a substance at the same time, improving detection efficiency of the apparatus.

Desirably, one or more thermal insulation pads 131 provided below the piston cylinder 128 and the absorption sieve drum use materials with low thermal conductivity, such as PTFE, PEEK, which effectively isolates thermal conduction between the thermal desorption chamber 132 and the adsorber during the sample absorption process, facilitating the sample absorption.

The thermal desorption chamber 132 is provided with a carrier gas shunting/sweeping interface 135. Once it cannot be received completely by the MCC column 136, the mixed sample gas is discharged at the shunting/sweeping interface 135. In addition, the shunting/sweeping interface 135 is completely opened to perform a sweeping operation to the thermal desorption chamber 132, so as to discharge the sample and impurities in the chamber, effectively reducing appearance of ghost peaks in a twice-sampling process. Meanwhile, a glass liner passage 133 with stable chemical property is hermetically embedded in the thermal desorption chamber 132. The liner passage 133 is replaceable periodically, which, on the one hand, prevents the sample gas from contacting and being reacted with metal material and thereby avoiding distortion of the detected sample and the detecting signal, and on the other hand, prevents large particulate matter from entering and blocking the chromatographic column.

According to embodiments, provision of the heating filter 115 not only obtains some volatile gas by heating the sample, especially solid particulate sample, and passes the gas through the semi-permeable membrane, but also prevents large particulate impurities from entering and blocking the passage. The semi-permeable membrane 117 can effectively prevent other contaminants including water molecules, ammonia molecules contained in the carrier gas from entering, so as to avoid pollution of the chromatographic column or the migration passage. In addition, the semi-permeable membrane can also prevent formation of clusters, improving resolution ratio of the apparatus.

According to embodiments, during the sampling process and the desorbing process, provision of a heat-resistant O-ring seal 127 effectively ensures a seal connection between a piston-type adsorber and a piston cylinder 128, to ensure sample collection efficiency and sample analysis efficiency. A thermal conductive sheath 137, on one hand, is used to protect the MCC 136, and on the other hand, is also provided with sealed interfaces for connection between the MCC and the thermal desorption chamber 132 and the double-mode ion mobility spectrometry 138. Meanwhile, it facilitates MCC heating insulation by an external heating circuit.

When the sample is pushed to the thermal desorption chamber for performing a thermal desorption, the roll-up door opens, the conveyor belt 103 operates, a baggage to be inspected (A) is conveyed out at the entrance door of the security inspection apparatus while another baggage to be inspected (B) is conveyed into the darkroom at the exit door of the security inspection apparatus. The X-ray generator emits ray beams, the L-shaped array of detectors receive the X-ray signal after transmission, and produce an image after being processed by the electronic and image processing parts. Once the baggage to be inspected is completely in the darkroom, the roll-up door closes again, and a tornado sampling assembly is formed, to begin another sampling. The operations are performed repeatedly, to achieve real-time collection and detection of a plurality of objects to be inspected.

According to embodiments, a method of inspecting an object to be inspected using a darkroom type security inspection apparatus is described. The method mainly comprises a sample collecting process, a sample treatment process, and a sample detecting process.

First is the sample collecting process. A baggage to be inspected is placed on the conveyor belt 103 of the safety-inspection apparatus and is conveyed to the darkroom. With infrared sensing control, front and back doors of the darkroom is switched from an open state to a closed state, and the conveyor belt 103 is decelerated or stopped. Air is blown, under the action of an air pump, from eddy flow holes arranged spirally around the darkroom to the baggage to be inspected, while a sampling suction nozzle located at the middle of the top of the darkroom and exhaust passages located at lateral sides of the top of the darkroom draw the air under the action of a high power air pump, in the darkroom. With the cooperation among the three, a tornado is formed. A solid small particulate sample adhered to surface of the baggage and gases released from one or more volatile or semi-volatile articles packed in the baggage passes through the heating filter and thus are heated. Some gases released from the solid small particulate sample and the volatile gaseous sample together pass through the semi-permeable membrane 117, and are suctioned, under the action of the sample suction pump, through the thermal insulation sampling passage and into a piston-type full-time pre-concentration and adsorption chamber, for performing a sample adsorption. Two piston-type adsorbers are used alternately to achieve full-time sample adsorption, and the sample suction pump performs a continuous gas suctioning to achieve a sample concentration.

Next is described the sample treatment process and the sample detecting process. The absorption sieve drum with an adsorbed and concentrated sample of the piston-type adsorber is pushed quickly into the thermal desorption chamber, the sample adsorbed to the adsorbent is instantly desorbed at high temperature, and the desorbed sample is mixed with the pre-heated chromatographic carrier gas from the bottom of the thermal desorption chamber and then is introduced to an analysis and detecting part (the MCC and the IMS) for performing the desorption of the sample.

According to one embodiment, the darkroom type security inspection apparatus comprises an overall chassis main body. The chassis main body comprises a conveyor belt, a housing, a gas guiding chamber, a thermal sleeve for the chamber, roll-up doors located at an entrance door conveyor belt and at an exit door conveyor belt and mounted with one or more eddy flow guiding plates 105, one or more eddy flow guiding plates 105 mounted at sides of the bottom of the chassis, a conveyor belt brace 104 embedded in both sides of the conveyor belt 103, an air suction hole at the top of the chassis, an inflating pump 112, an exhaust pump 114, an inflation passage, an exhaust passage, a heating filter, a sample collecting passage, a gas guiding chamber, a semi-permeable membrane 117 together with its clamping elements, a top tundish-shaped cover, and the like.

The conveyor belt 103 is controlled by a variable speed motor and is used for conveying the baggage to be inspected through the darkroom. Once the baggage to be inspected is placed on the conveyor belt, the belt transfers the baggage to be inspected to the darkroom. When it is detected by the infrared sensing assembly mounted at a lateral wall of the chassis adjacent to the entrance door that the baggage to be inspected is completely in the interior of the chassis, the reducing motor starts to reduce the speed or to stop the operation (namely, the conveyor belt 103 is decelerated or stopped), the roll-up doors at the entrance door and the exit door of the security inspection apparatus are rolled down, to form a closed darkroom in the chassis. After the X-ray detection unit performs a scan on the object 108 to be inspected, an image of the object 108 to be inspected is displayed, in order to inspect whether or not one or more prohibited items are contained within the object 108 to be inspected, and also to determine the position of the object 108 to be inspected. Once the object 108 to be inspected arrives at the expected position, a further inspection on the object 108 to be inspected can be performed. Here, the eddy flow guiding plate 105 distributed on side walls of the chassis and the eddy flow guiding plates located at the roll-up doors adjacent to the entrance door and the exit door just form a whole circle, and a plurality of loops of the eddy flow holes arranged in a spiral form on the eddy flow guiding plate are also provided. The pump 112, the pump 114 and the sample suction pump start to operate, and air from the inflatable pump 112 passes though the passages within the housing of the chassis and is discharged at eddy flow holes arranged in a spiral form of the bottom of the chassis, to form a spiral air flow. The formed spiral air flow is pulled up by the exhaust pump and the sample suction pump at the top of the chassis, to form a strong tornado. Under the action of strong suction action of the tornado, a solid small particulate sample adhered to surface of the baggage and trace gas released from a volatile or semi-volatile article packed in the baggage are passed through the heating filter at the upper portion of the gas guiding chamber. A gaseous sample of a volatile article is passed through the semi-permeable membrane 117 directly under the action of the tornado gas flow, and then is introduced through the thermal insulation sample collecting passage to the adsorber, for performing a sample adsorption and collection. The solid small particulate sample adhered to surface of the baggage, which is suctioned by the tornado, is firstly heated rapidly between the heating filter and the semi-permeable membrane 117 to release some gaseous sample, then the released gaseous sample is passed through the semi-permeable membrane 117, and is introduced through the thermal insulation sample collecting passage to the adsorber, while the solid particulate residues are discharged by the exhaust pump 114, preventing them from polluting the passages or adversely affecting detection of a next baggage to be inspected. Both the pump 112 and the pump 114 are used to provide continuous circulating winds for generation of the tornado. The power of the pump 112 may be chosen in accordance with requirements. Due to the gas amplification action of the tornado, flow velocity of the exhaust pump 114 is 10 times or more than the inflating pump 112, so that a negative pressure is formed to facilitate adsorption of the sample. In order to avoid the air flow from the pump 112 disturbing the sample suctioned from the sampling target, on the one hand, the air source for the air flow from the inflatable pump 112 is located away from the sampling target as far as possible, for example, a flexible soft tube is adopted to set apart the pump from the sampling port, and on the other hand, the air flow from the pump 112 is filtered and purified, to avoid cross contamination among the gases, improving sensitivity of the sampling operation of the apparatus.

The gas guiding chamber can be heated. The thermal sleeve for the chamber is used for thermal insulation of the whole gas guiding chamber as well as the inflation passage between the gas guiding chamber and the thermal sleeve. Generally, the temperature in the gas guiding chamber or in the darkroom may be set to be 10-20 degrees Celsius higher than room temperature, on the one hand, achieving safety, and on the other hand, promoting rapid volatilization of highly volatile or volatile prohibited items packed in the baggage, thereby facilitating the sample collection.

Conveyor belt braces 104 are provided specially at both sides of the conveyor belt 103. Dense bristles are adopted in a portion of the brace 104 contacting the conveyor belt 103. The braces 104 as well as its bristles ensure that the darkroom is sealed in an optimal manner when performing a tornado sampling process, preventing the detection from being adversely affected due to a large amount of air flow from the bottom of the belt.

The semi-permeable membrane 117 is clamped by two metal sheets which, on the one hand, are used for fixation of the semi-permeable membrane 117 and, on the other hand, can prevent the semi-permeable membrane 117 to be torn under the action of the strong tornado. Material for the semi-permeable membrane 117 can prevent other contaminants including water molecules, ammonia molecules contained in the carrier gas from passing through, so as to avoid pollution of the chromatographic column or the migration passage. In addition, the semi-permeable membrane can also prevent formation of clusters, improving the resolution ratio of the apparatus.

According to one embodiment, the sample collecting connection passage is made of metal, chemically stable fluorine rubber or Teflon. The wall of the passage can be provided with a heating film and insulation cotton. During the entire sample collection process, the sample collecting connection passage is maintained at high temperature (100-250 degrees Celsius), which effectively eliminates sample loss or passage contamination caused by sample condensation to the inner wall of the passage.

According to one embodiment, the full time pre-concentration sampler mainly includes a double piston cylinder, a piston-type absorber, and a heat-resistant O-ring seal for the sealing between the piston cylinder and the piston-type adsorber. Desirably, the double piston cylinder is manufactured of PTFE or PEEK material with good thermal insulation properties, good mechanical properties and stable chemical properties. The heat-resistant O-ring seal is used for the sealing between the piston cylinder and piston-type adsorber. The absorber piston mainly consists of a piston rod body in an upper part of the adsorber, an adsorber sieve drum in the middle part of the adsorber and a thermal insulation pad located in the bottom part of the adsorber. Desirably, the piston rod is made of PTFE and is driven by the motor. During the sample collection and sample analysis, the electrode can drive the piston-type absorber to be movable hermetically between the piston cylinder and the thermal desorption chamber. The adsorber sieve drum, desirably, is made of chemically stable inert metal, and adsorbent can be placed inside the hollow sieve drum. Diameter of the adsorbent materials should be greater than diameter of outer wall of the sieve drum passage. The adsorbent material can be added according to demands of user's main detection target. The thermal insulation pad, Desirably, is made of PTFE material with good thermal insulation properties and stable chemical properties. The thermal insulation pad can effectively isolate thermal exchange between the thermal desorption chamber and the absorption sieve drum, facilitating adsorption and concentration of the sample. The thermal insulation pad and the absorption sieve drum are connected by screws, which facilitates replacements of the thermal insulation pad and of adsorbent materials. During a detecting process, two piston-type adsorbers are used alternately to achieve full-time sample adsorption, improving detection efficiency of the apparatus.

According to one embodiment, the thermal desorption chamber is coated with a heating film for heating the chamber. Meanwhile, insulation cotton is coated outside the heating film for thermal insulation of the chamber. A temperature sensor 123 is further installed on the chamber and is for real-time monitoring and controlling temperature inside the chamber through an external temperature control circuit. Temperature programmed mode is used in the thermal desorption chamber as well as the abovementioned passage heating assembly, which can effectively reduce the power consumption. During the sampling desorbing process, one piston-type adsorber with adsorbed and concentrated sample is pushed quickly under the driving of the motor into the thermal desorption chamber at high temperature, at the same time, another piston-type adsorber with desorbed and detected sample is pulled out under the driving of the motor and waits for adsorption and concentration of sample of next baggage to be inspected. The sample adsorbed to the piston-type adsorber which is pushed into the thermal desorption chamber is instantly desorbed and then is mixed with the carrier gas from bottom of the thermal desorption chamber, after that, it is introduced to a chromatographic column for performing a pre-separation, finally, it is introduced to the IMS for performing a detection.

According to one embodiment, the use of porous capillary columns (MCC) with small volume, high column efficiency and rapid separation speed can overcome problems existing in conventional capillary column, including long time (10-15 minutes) analysis, requirements on large volume furnace for high temperature demand, to meet requirements on the rapid on-site detection.

According to one embodiment, the temperature-control assembly comprises a heating system, a temperature control system, a thermal insulation unit, temperature sensor and a temperature control circuit. This assembly is mainly used for the heating, heat insulation and temperature control of the sample collecting connection passage, the gas guiding chamber, the heating filter, the thermal desorption chamber, the chromatographic column and the ion migration passage. Desirably, the sample collecting pipe thermal, the desorption and the migration passage are heated by the heating film, the gas guiding chamber is heated by a heating rod or a heating blanket, and the heating net is heated by heating wires with fast heating property. Desirably, the thermal insulation unit uses insulation cottons, which are mainly used together with the temperature-control assembly, for thermal insulations of these temperature-control devices, on the one hand, reducing temperature difference between different locations or parts and improving accuracy of the detection, on the other side, reducing the overall energy consumption.

According to one embodiment, the ion mobility spectrometry is in a positive and negative double-mode. The positive and negative double-mode ion mobility spectrometry can achieve on-site detections on positive and negative ions from the baggage to be inspected at the same time. Compared with the single mode, it needs no switching on electric field, shortens the detection time, and improves the detection efficiency. In addition, the migration passage is made of high temperature resistant ceramic materials, greatly broadening the range of the samples to be detected.

The apparatus described herein can have one or more of the following advantages.

The apparatus uses a closed tornado sampling assembly which is capable of performing a full sampling on a baggage to be inspected. Meanwhile, because the tornado sampling way has strong suctioning force, it can greatly improve collection efficiency on volatile or semi-volatile samples in the baggage or solid particulate sample adhered to surface of the baggage, to achieve a direct sampling on volatile or semi-volatile matters in the baggage or surface contamination solid matters without unpacking the baggage.

This darkroom type baggage security inspection apparatus can perform a concentration on the collected sample during detection of the sample, reduce the detection limit of requirements of IMS detector, reduce difficulty of development of the apparatus and cost of the apparatus, realize the positive and negative ion detection at the same time to establish a correlation between positive and negative maps, and improves the detection speed compared with a single mode. This darkroom type baggage security inspection apparatus adopts full-time pre-concentrated sample collection technology, which can greatly enhance the sampling efficiency and improve detection efficiency of the apparatus.

Compared with routine X-ray based baggage security inspection apparatus, the described darkroom type baggage security inspection apparatus has improved detection sensitivity on volatile or semi-volatile prohibited items carried in baggage, can accurately inform of species of prohibited items without unpacking, and can also perform an inspection of other items on the object to be inspected. The described darkroom type security inspection apparatus has a unibody construction and performs a much more complete inspection.

Although several exemplary embodiments of the present invention have been shown and described, it would be appreciated by those skilled in the art that various changes or modifications may be made in these embodiments without departing from the principles and spirit of the present invention, the scope of which is defined in the claims and their equivalents.

What is claimed is:

1. A darkroom type security inspection apparatus comprising:
    a housing constituting a closed darkroom, and
    assemblies disposed inside the housing, the assemblies disposed inside the housing comprise:
    a sampling assembly comprising:
        a sample collecting unit configured to collect a sample,
        a conveyor unit configured to convey an object to be inspected from outside into the sample collecting unit, and
        a X-ray detection unit to detect a position of the object to be inspected, wherein the X-ray detection unit is configured to determine the position of the object to be inspected within the sampling assembly so that the object to be inspected is conveyed to an expected position;
    a sample processing assembly configured to concentrate and desorb the sample; and
    a sample inspecting assembly configured to inspect composition of the sample,
    wherein the sampling assembly, the sample processing assembly and the sample inspecting assembly are communicated by fittings so that collection, processing and inspection of the sample are performed on the object to be inspected, that has been conveyed into the housing constituting the closed darkroom, within the housing,
    wherein the sample collecting unit comprises a sampling chamber having a first end and a second end opposite to the first end, the conveyor unit is located at the first end so that the object is at least partly within the sampling chamber, and the sampling chamber further comprises a sample outlet adjacent to the second end and configured to discharge the sample,
    wherein the sampling chamber further comprises an inflation port and an exhaust port formed at an inner wall of the sampling chamber, the inflation port is configured to introduce a gas flow and the exhaust port is configured to discharge the gas, to produce a tornado type gas flow within the sampling chamber, and the tornado type gas flow moves spirally from the first end to the second end of the sampling chamber so that the sample carried by the object to be inspected is conveyed by the tornado type gas flow to be nearby the second end, and
    wherein the conveyor unit comprises a conveyor belt brace made of deformable material and a conveyor belt, and the apparatus is configured to produce a negative pressure within the housing constituting the closed darkroom, when the conveyor belt does not move, so that the conveyor belt brace is deformed to form a seal together with the conveyor belt.

2. The darkroom type security inspection apparatus according to claim 1, wherein the X-ray detection unit comprises a X-ray generator configured to emit X ray radiation, detectors configured to detect the X ray radiation and a display, wherein the X-ray detection unit is configured to detect the remaining X-rays passing through the object to be inspected so as to display both the position of the object to be inspected within the sampling assembly and contents inside the object to be inspected.

3. The darkroom type security inspection apparatus according to claim 1, wherein the sampling assembly comprises a heating filter configured to filter the sample conveyed toward the second end, and to heat the sample to be inspected so as to facilitate volatilization of the sample.

4. The darkroom type security inspection apparatus according to claim 1, wherein the sampling assembly comprises a semi-permeable membrane configured to selectively filter the sample, and the semi-permeable membrane is disposed within the sampling chamber to separate a space for mixture with carrier gas.

5. The darkroom type security inspection apparatus according to claim 1, wherein the sample processing assembly comprises a pre-concentrated sample adsorber comprising an absorption sieve drum configured to concentrate the sample and a piston rod configured to deliver the sample in the absorption sieve drum using a piston; and
    a thermal desorption chamber configured to desorb the sample in the absorption sieve drum at high temperature and to mix the sample with suitable carrier gas.

6. The darkroom type security inspection apparatus according to claim 1, wherein the sample inspecting assembly comprises porous capillary columns configured to pre-separate the sample, and an ion mobility spectrometer.

7. A method of inspecting an object to be inspected using a darkroom type security inspection apparatus according to claim 1, the method comprising:
    placing the object to be inspected on the conveyor unit, and conveying the object to be inspected into the darkroom type security inspection apparatus via the conveyor unit; and
    implementing an inspection on the object to be inspected using the darkroom type security inspection apparatus.

8. The darkroom type security inspection apparatus according to claim 1, wherein the sample inspecting assembly is configured to inspect composition of the sample by means of a gas chromatographic-ion mobility spectrometer or a separated ion mobility spectrometer.

9. A darkroom type security inspection apparatus comprising:
    a housing constituting a closed darkroom, and
    assemblies disposed inside the housing, the assemblies disposed inside the housing comprise:
    a sampling assembly comprising:
        a sample collecting unit configured to collect a sample, a conveyor unit configured to convey an object to be inspected from outside into the sample collecting unit, and
a X-ray detection unit to detect the object to be inspected;
a sample processing assembly configured to concentrate and desorb the sample; and
a sample inspecting assembly configured to inspect composition of the sample,
wherein the sampling assembly, the sample processing assembly and the sample inspecting assembly are communicated by fittings so that collection, processing and inspection of the sample are performed on the object to be inspected, that has been conveyed into the housing constituting the closed darkroom, within the housing,
wherein the sample collecting unit comprises a sampling chamber having a first end and a second end opposite to the first end, the conveyor unit is located at the first end so that the object is at least partly within the sampling chamber, and the sampling chamber further comprises a sample outlet adjacent to the second end and configured to discharge the sample,
wherein the sampling chamber further comprises an inflation port and an exhaust port, the inflation port is configured to introduce a gas flow and the exhaust port is configured to discharge the gas, to produce a gas flow within the sampling chamber, and the gas flow moves spirally from the first end to the second end of the sampling chamber so that the sample carried by the object to be inspected is conveyed by the gas flow to be nearby the second end, and
wherein the inner wall of at least a part of the sampling chamber is formed in a frustoconical shape having a smaller-diameter round end adjacent to the first end and a larger-diameter round end adjacent to the second end.

10. The darkroom type security inspection apparatus according to claim 9, wherein the X-ray detection unit is configured to detect and determine a position of the object to be inspected within the sampling assembly so that the object to be inspected is conveyed to an expected position.

11. The darkroom type security inspection apparatus according to claim 9, wherein the conveyor unit of the sampling assembly comprises a conveyor belt and a conveyor belt brace, edges of both sides of the conveyor belt and the conveyor belt brace are configured to be a matching structure so that the conveyor belt brace allows the conveyor belt to move but forms a seal together with the conveyor belt when the conveyor belt does not move.

12. The darkroom type security inspection apparatus according to claim 9, wherein the conveyor unit comprises a conveyor belt brace made of deformable material and a conveyor belt, and the apparatus is configured to produce a negative pressure within the housing constituting the closed darkroom, when the conveyor belt does not move, so that the conveyor belt brace is deformed to form a seal together with the conveyor belt.

13. The darkroom type security inspection apparatus according to claim 9, wherein the inflation port is configured so that an axially inflating direction of the inflation port is essentially tangent with an inner surface of an inner wall of the chamber and is inclined towards the sample outlet side.

14. The darkroom type security inspection apparatus according to claim 9, wherein the sampling assembly comprises a heating filter configured to filter the sample, and to heat the sample to be inspected so as to facilitate volatilization of the sample.

15. The darkroom type security inspection apparatus according to claim 9, wherein the sampling assembly comprises a semi-permeable membrane configured to selectively filter the sample, and the semi-permeable membrane is disposed within the sampling collecting unit to separate a space for mixture with carrier gas.

16. The darkroom type security inspection apparatus according to claim 9, wherein the sample processing assembly comprises a pre-concentrated sample adsorber comprising an absorption sieve drum configured to concentrate the sample and a piston rod configured to deliver the sample in the absorption sieve drum using a piston; and
a thermal desorption chamber configured to desorb the sample in the absorption sieve drum at high temperature and to mix the sample with suitable carrier gas.

17. The darkroom type security inspection apparatus according to claim 9, wherein the sample inspecting assembly comprises porous capillary columns configured to pre-separate the sample, and an ion mobility spectrometer.

18. A darkroom type security inspection apparatus comprising:
a housing constituting a closed darkroom, and
assemblies disposed inside the housing, the assemblies disposed inside the housing comprise:
a sampling assembly comprising:
a sample collecting unit configured to collect a sample,
a conveyor unit configured to convey an object to be inspected from outside into the sample collecting unit, and
a X-ray detection unit to detect the object to be inspected;
a sample processing assembly configured to concentrate and desorb the sample; and
a sample inspecting assembly configured to inspect composition of the sample,
wherein the sampling assembly, the sample processing assembly and the sample inspecting assembly are communicated by fittings so that collection, processing and inspection of the sample are performed on the object to be inspected, that has been conveyed into the housing constituting the closed darkroom, within the housing,
wherein the conveyor unit comprises a conveyor belt and a conveyor belt brace, edges of both sides of the conveyor belt and the conveyor belt brace are configured to be a matching structure so that the conveyor belt brace allows the conveyor belt to move but forms a seal together with the conveyor belt when the conveyor belt does not move,
wherein the conveyor belt brace is made of deformable material, and
wherein the apparatus is configured to produce, when the conveyor belt does not move, a negative pressure within the housing constituting the closed darkroom so that the conveyor belt brace is deformed to form the seal.

19. The darkroom type security inspection apparatus according to claim 18, wherein the sample collecting unit comprises a sampling chamber having a first end and a second end opposite to the first end, the conveyor unit is located at the first end so that the object is at least partly within the sampling chamber, and the sampling chamber further comprises a sample outlet adjacent to the second end and configured to discharge the sample, and wherein the sampling chamber further comprises an inflation port and an exhaust port, the inflation port is configured to introduce a gas flow and the exhaust port is configured to discharge the gas, to produce a gas flow within the sampling chamber, and the gas flow moves from the first end to the second end of the sampling chamber so that the sample carried by the object to be inspected is conveyed by the gas flow to be nearby the second end.

20. The darkroom type security inspection apparatus according to claim 19, wherein the inner wall of at least a part of the sampling chamber is formed in a frustoconical shape having a smaller-diameter round end adjacent to the first end and a larger-diameter round end adjacent to the second end.

* * * * *